United States Patent [19]

Huang et al.

[11] 4,191,892
[45] Mar. 4, 1980

[54] SPREAD BEAM OVERLAP METHOD

[75] Inventors: Sung-Cheng Huang, Sherman Oaks, Calif.; Carl J. Brunnett, Mayfield Heights; Rodney A. Mattson, Mentor, both of Ohio

[73] Assignee: Picker Corporation, Cleveland, Ohio

[21] Appl. No.: 921,010

[22] Filed: Jun. 30, 1978

[51] Int. Cl.² ................ G01N 21/34; G01N 23/04
[52] U.S. Cl. .................. 250/445 T; 250/360
[58] Field of Search ............. 250/445 T, 360

[56] References Cited
U.S. PATENT DOCUMENTS

4,084,093  4/1978  Marsh et al. ............ 250/445 T

Primary Examiner—Alfred E. Smith
Assistant Examiner—Thomas P. O'Hare
Attorney, Agent, or Firm—Watts, Hoffmann, Fisher & Heinke Co.

[57] ABSTRACT

An improved method for computed tomographic scanning is disclosed. A beam of electromagnetic radiation subtending an angle $\phi$ is alternately translated and rotated past a patient. The intensity of the beam is detected by an array after the radiation passes the patient and a reconstructed image created from the detected intensities. Each rotation of the array is through an angle less than the angle $\phi$ subtended by the array producing redundant intensity readings for similarly oriented beam paths through the patient. This redundant intensity data is modified according to a scheme which tends to reduce motion and misalignment artifacts within the patient.

8 Claims, 9 Drawing Figures

SPREAD BEAM OVERLAP METHOD

BACKGROUND OF THE INVENTION

This invention relates generally to transmission computed tomography, and more particularly, relates to an improved image construction processing technique to provide a visualization of an internal planar section of a subject. The improved re-construction process involves techniques which tend to reduce motion and misalignment artifacts on the visualization.

FIELD OF THE INVENTION

A conventional radiograph is a two-dimensional shadow image of a three-dimensional subject. The depth dimension is not apparent because all interior portions of the patient are imaged in a single plane. As a consequence, a conventional radiograph often fails to provide necessary detail as to spatial location of a condition, and may not reveal that condition's existence within the patient.

Computed tomographic procedures have been developed to fulfill some objectives which are unobtainable by conventional radiograph procedures. In computed tomography, an image of a cross-sectional plane of a subject is developed by sequentially directing radiation through the subject from a plurality of origins.

According to one type of transverse section tomography, called transmission scanning, X-radiation detectors are supported each in alignment with a different highly collimated beam of radiation generated by an X-radiation source. The beams are assumed to be for purposes of discussion in a plane and their axes are coplanar. The radiation source and detectors are moved relative to the subject. The beams are positioned such that they pass through the subject with their axes lying within the plane containing the section of the subject to be examined.

In a majority of existing computed tomography machines, the relative motion of source and detectors is a combination rectilinear and orbital motion. The combined translational and rotational movement is called TR scanning and is usually accomplished with a set of individual beams of radiation. The intensity of each beam is detected and recorded after it has passed through the subject. The paths are spaced from one another by predetermined angular increments and are oriented in a plane and extending at predetermined angles about a central axis intersecting the plane.

Passage of consecutive moving beams of radiation through a subject in a particular angular orientation about a central axis is said to be data coming from a particular "pass". The angular orientation of the source and detectors about a central axis is incremented after each pass and before another pass is obtained. This process continues until a predetermined number of passes have been performed and the sets of collected intensity data have been stored.

One type of translate-rotate source produces a plurality of non-parallel beams of X-radiation. The intensities of those non-parallel beams are detected after they have passed through a subject and as the source and detectors translate relative to the subject. Since the beams are not parallel to one another, sequential detection of the intensities of adjacent beams during a particular pass does not provide intensity data from paths traveling parallel to each other. Those mathmatical reconstruction techniques known within the art which are in current use require, however, the utilization of intensity data from parallel paths. Accordingly, the data representing the detected intensities from angularly spread beam arrangements must be rearranged if it is to be analyzed according to well known reconstruction techniques.

The detected intensities of the beams are utilized for computing X-ray transmission or X-ray absorption characteristics of the scanned section of the patient. The transmission data are then utilized to provide a density variation mapping of the internal structure of the patient in the scanned plane. In a translate-rotate configuration during the time the source of radiation is rotated from one orientation to another, no intensity information is being obtained. It is possible that movements within the patient will produce what is known within the art as motion artifacts. These motion artifacts appear on the final image as streaks and do not represent structure within the patient.

In a typical medical diagnostic application, the scanner is used to scan a cross-section of a human patient. Regardless of how quiet the patient is kept, breathing and motion of internal organs produce the above mentioned motion artifacts. Artifacts can also result from discontinuities in beam intensity while the source is being repositioned for making a different pass of the patient.

In a translate-rotate environment in which the source is rotated a finite number of degrees, misalignments of data are possible. To obtain continuous views of the patient it is necessary that the rotation be controlled so that the beam spread in one orientation abuts with the beam spread in a different rotated configuration. If there is error in this rotation, the beam will not cover certain orientations and no intensity data will be obtained for those orientations. This motion misalignment of the detector mechanism produces discontinuities in data availability which introduce artifacts similar to the motion artifacts mentioned previously.

PRIOR ART

Prior proposals for computed tomography scanning systems have sought to deal with the problems of motion artifacts and imprecise rotation artifacts with varying degrees of success. Decreasing the scan time for a particular slice of patient minimizes the adverse effects caused by patient motion. The problems of misrotation have been minimized by using precise mounting and source motion techniques to assure the beams properly abut one another. While these techniques have helped reduce the artifacts, neither approach has eliminated those artifacts since regardless of the speed of rotation there will be some motion in the patient and the beam mounting and rotating techniques have not completely eliminated data misalignment.

SUMMARY OF THE INVENTION

The present invention provides a new and improved method for reducing misalignment and motion artifacts in a computed tomographic scanner. Essentially redundant radiation intensity for similarly oriented beam paths is obtained during different times in the cross-sectional scan. During the reconstruction process in which images are obtained, the two readings from similar paths each contribute to the reconstruction process for those paths. In a spread beam scanner, this multiple data is obtained by allowing the angular spread over which data is collected in one translation to overlap the angular spread over which data is collected during the previous translation so that successive data collection translations produce redundant intensity data. The beam overlap technique does not require precise source rotation to obtain continuous data readings and the combining of the two different data readings produced during different translations of the scan reduces the effects of patient motion.

The new technique includes the steps of providing a source of a set of beams of electromagnetic radiation that subtends a given angle. The beam spread is translated past the patient along a given path. During this translation, beam intensities for various orientations are obtained by a series or array of detectors. After the initial translation, the source and detectors are rotated through an increment of an orbit whose angle is less than the angle subtended by the beam set. The source and detectors are then translated again to obtain a second pass of the patient. Since the orbital increment through which the beam set is rotated is less than the angle it subtends, during the second pass some detectors in the detector array record beam intensities for beam paths that overlap those that have already been measured during the initial pass. This redundant data is scaled to produce a modified beam intensity for those orientations. This modified beam intensity is utilized in a reconstruction algorithm to provide density information within the patient.

The scaling of redundant data to provide modified intensity values for a portion of the computer tomography scan helps eliminate discontinuities caused either by inaccurate incremental rotation of the source or by patient motion. This is true because the detected intensity before rotation and the intensity after rotation both contribute to the reconstruction algorithm for a given beam to thereby reduce the adverse image artifacts which would otherwise be present.

Since beam overlap and redundant data is utilized, precise control of the extent of an incremental orbit is not required. As a result a simplified, inexpensive, and reliable rotational control system is employed.

In the disclosed and preferred translate-rotate scanner, the beam set subtends an angle of 20.5°. By indexing the beam source through an angle which is nominally 20° during the rotate portion of the scan, a beam overlap of about $\frac{1}{2}$° or more occurs between each successive pair of translations. Thus, during a second scan at least one beam of the set travels over an identical or substantially identical path as that traversed by another beam of the set during the preceding pass.

Depending upon the dimension of the beam set and the number of translations deemed desirable, the amount of beam overlap can be varied. Larger amounts of beam overlap help better reduce motion artifacts than small overlaps, but tend to increase the amount of scan time.

A technique for modifying or averaging the multiple intensity readings within an overlap portion has been developed which permits variations in the amount of beam set overlap. The position of an individual beam orientation within the overlap is also taken into account in determining how the multiple beam intensity readings are to be modified. Typically, the two identical path intensities are multipled by scaler weighting factors and then used in the reconstruction process. The weighting factors vary within the overlap portion, according to whether two sets of data were developed along identical or closely spaced beam paths. While the two weighting factors vary, for any given overlap orientation they produce constant data density with respect to angular position. In a back projection step in the reconstruction algorithm, each set of data is back projected at its actual angular orientation.

If data is collected only over a total angular range of 180°, then any patient motion that occurs between the first and last pass (i.e. beginning and end of data collection) produces a rather intense motion artifact. To reduce this artifact the source and detector are rotated more than 180° about the patient. Once subsequent translations and rotations have scanned 180° of spatial orientations, the X-ray beam begins to scan through orientations previously scanned but in an opposite direction. These overscan beam intensity readings as well as the previous readings which cover substantially the same paths, are scaled by a similar process in order to reduce motion artifacts.

These scaling techniques as well as other features and advantages of the invention will become more apparent as the invention becomes better understood from the detailed description that follows, when considered in conjunction with the accompany drawings.

DETAILED DESCRIPTION OF THE INVENTION

Figure 1:
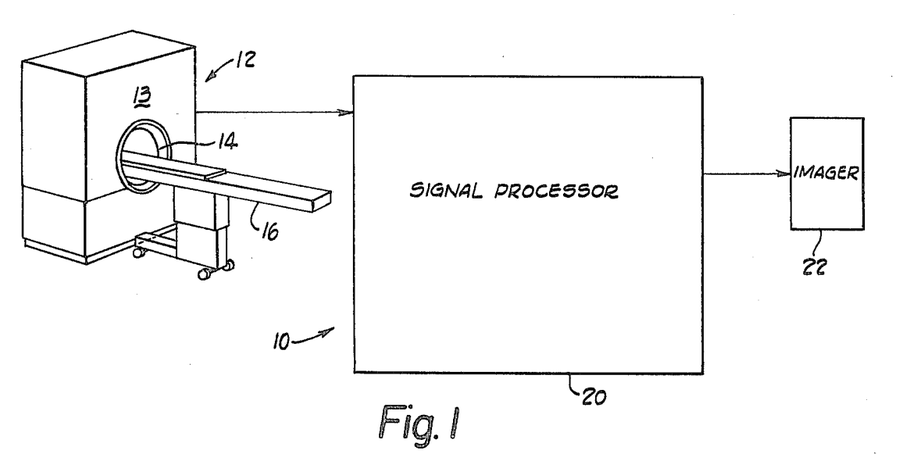
FIG. 1 shows a tomographic scanning system in schematic form.

FIG. 1 shows a computed tomography system 10 used for examining the internal structure of a patient. The unit comprises a scanning unit 12, a couch 16, a signal processor 20 and an imager 22.

The scanning unit 12 is mounted to a floor and remains stationary relative to the patient. The scanning unit includes a housing 13 which covers X-ray apparatus and provides an attractive appearance to both the patient and the doctor. The housing 13 is constructed to include an aperture 14. The couch 16 is movably mounted and is operative to position the patient within the aperture 14 for X-ray scanning.

The signal processor 20 and the imager 22 are electrically connected to the scanning unit. The scanning unit obtains X-ray intensity data and sends this intensity data to the signal processor. The X-ray intensity data is then processed by the signal processor to obtain information concerning the relative densities of the cross-section of the patient. This intensity or density data is then transferred to the imager where the doctor can view relative density information on a viewing screen.

Figure 2:
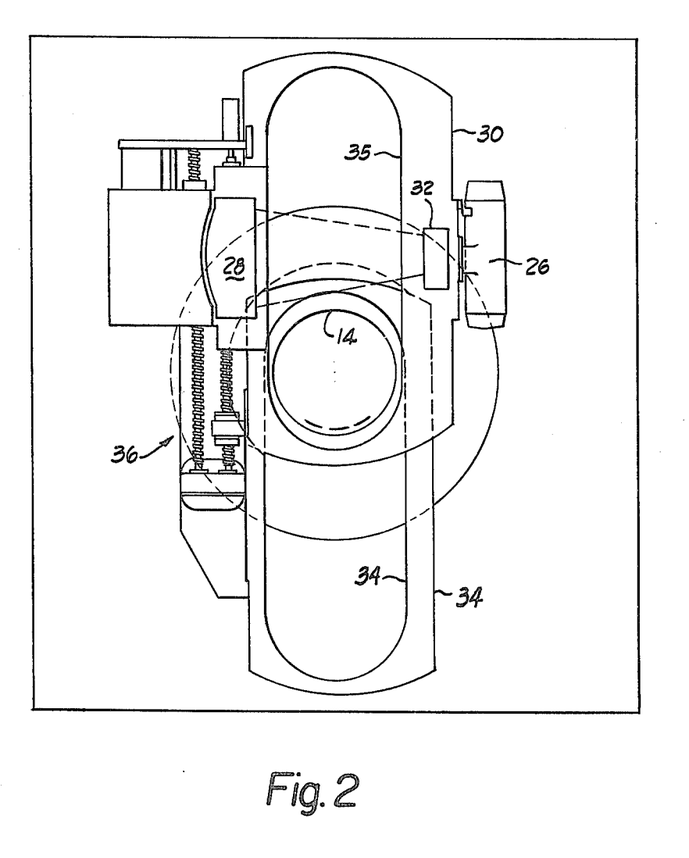
FIG. 2 shows a front plan view of the scanning apparatus.

Shown in FIG. 2 is the internal structure of the scanning unit 12 without the housing. The apparatus of FIG. 2 includes an X-ray source 26, a detector 28, a collimator 32 and a source/detector mounting structure 30. The collimator 32 shapes the X-ray beam into a number of individual equally spaced beam paths. The X-ray source 26 and the collimator 32 operate in conjunction to send the beam of X-rays to the detector 28. The source/detector mounting structure 30 is attached to a worm gear drive mechanism 36 which imparts translational motion to the combined source and detector.

To scan the patient with X-rays, the worm drive mechanism imparts a translational motion to the source and detector causing the fan beams to cross the patient aperture 14. As the beams cross the aperture, the detectors measure X-ray intensity and send signals to the signal processor.

Also seen in FIG. 2 is a counter weight 34 mounted within the scanning unit and attached to the worm drive mechanism 36. When the worm drive mechanism causes the source and detector to move in one direction, it also causes the counter weight 34 to move in an opposite direction. This counter weight 34 insures that the scanning unit is maintained in proper balance when rotational motion to be described hereinafter, is imparted to the unit.

The source/detector mounting structure 30 and the counter weight 34 include elongated apertures 35, 38 respectively. These apertures are sized to permit translational motion of the counter weight and the source/detector mount without interference with the patient aperture.

Figure 3:
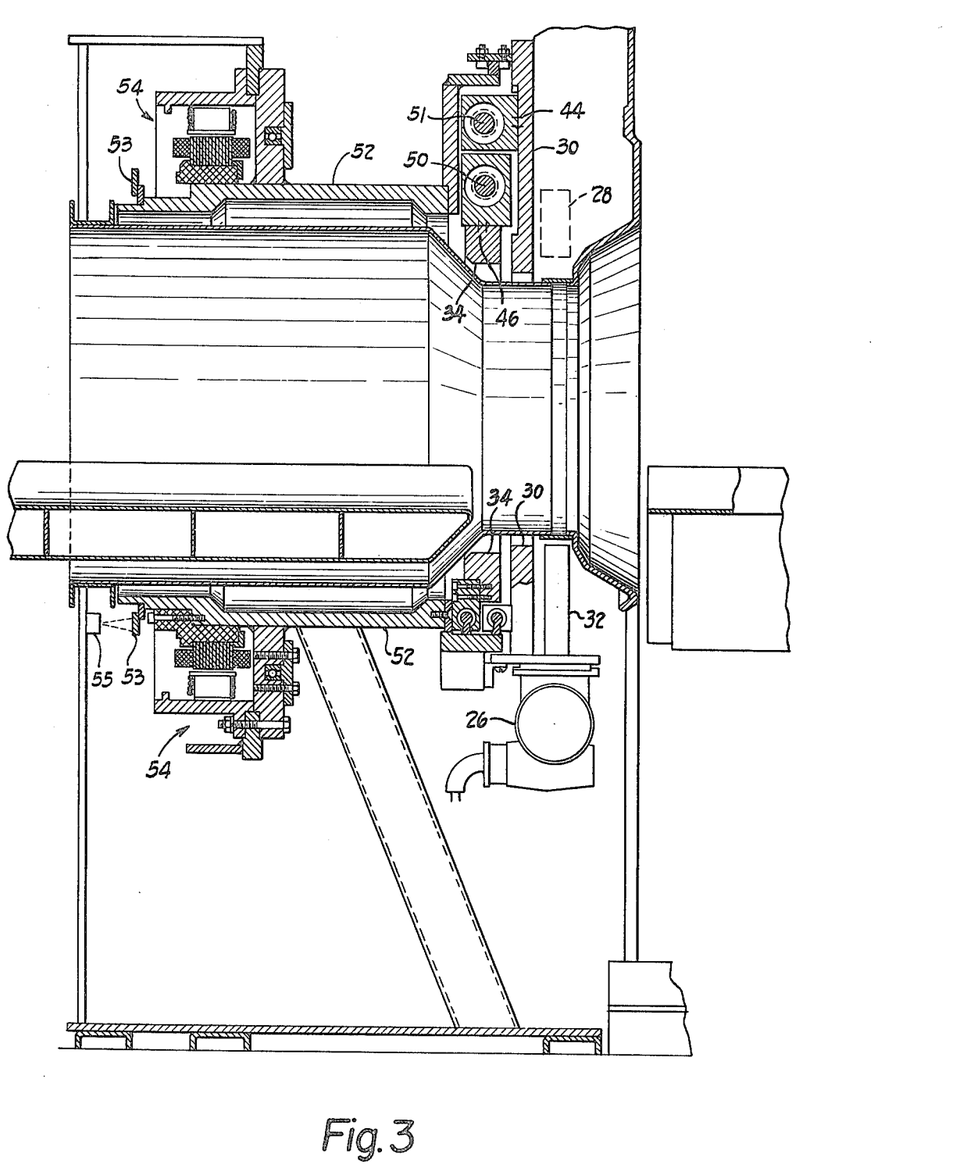
FIG. 3 shows a side sectional view of the apparatus of FIG. 2.

FIG. 3 depicts the apparatus of FIG. 2 as shown from a side view. The source detector mount 30 is shown attached to the worm mechanism 36 by two fasteners 44. The counter weight 34 is shown attached to the worm mechanism by means of a second set of fasteners 46. The worm mechanism moves the counter weight parallel to a first translational axis 50 and the source/detector mount 30 parallel to a second translational axis 51. When the source detector pair is moving in one direction, the counter weight is moving in an opposite direction.

The source of X-rays, the detector, the mounting structure, the counter weight, and the worm mechanism are all mounted for rotational motion about an axis coincident with the axis of the patient aperture. As seen in FIG. 3, all of these elements are directly attached to a rotating gantry 52 which is driven by a motor 54. The motor causes the gantry to rotate about the patient aperture axis thereby causing the source and detector to rotate about the same axis.

Mounted to the gantry 52 is circular ring 53 containing 18,000 equally spaced markings. As these markings move past a photo detector 55, the photo detector records the position of the gantry relative to a fixed reference frame. This information is transmitted to the signal processor so that the processor knows the angular orientation of the source/detector pair to the nearest 0.01 degree for each pass of the field.

From FIGS. 2 and 3 it is apparent that the source and detector are mounted for both translational and rotational motion. A typical scanning movement therefore includes first a translation and then a rotation followed by subsequent translations and rotations until the beam set has traversed the patient in a variety of directions. The X-ray intensity data from the detectors is then sent to the signal processor for reconstruction imaging. Reconstruction imaging is known within the art and will be described only in enough detail to enable one skilled in the art to practice the present invention.

Figure 4:
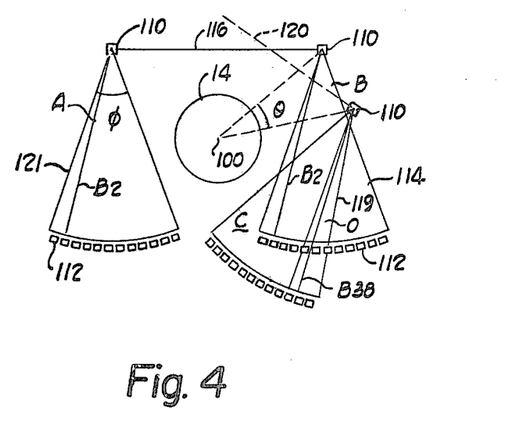
FIG. 4 schematically shows translational and rotational motion of a source and detector array.

Shown in FIG. 4 is a schematic representation of a source and detector array being translated and subsequently rotated about a patient axis 100. Position A indicates the source 110 and the detector array 112 positioned relative to the patient aperture 14 before the beginning of a typical computed tomography scan. The collimator and other mounting structure has been eliminated for ease of representation. The array of X-ray beams subtends angle $\phi$ and is incident upon a detector array. The detector array is shown schematically but typically comprises 41 individual X-ray detectors of any suitable design. These individual detectors send X-ray beam intensity data to the signal processor for reconstruction processing. The scan begins when the worm mechanism of FIG. 2 drives the source/detector past the aperture 14 thereby sending the set of X-ray beams through the patient. The source 110 moves along a straight line path 116 until it arrives at an orientation B. The connected detector array 112 concurrently moves along a straight line path until it arrives at an orientation B. At the beginning of this translational movement, the X-ray beam intersects no portion of the aperture and after the translational motion, the X-ray beam has passed completely across the aperture.

As the source and detector array are moved relative to the aperture, X-ray intensity data is being collected by each of the detectors in the array. In that preferred arrangement the array includes 41 detectors which are continuously sending signals to the image processor at regular intervals throughout the translation.

In order to scan the patient aperture from a variety of different angles, the source/detector must be rotated by the motor 54 shown in FIG. 3. Once the translation is completed, the motor causes the source and detector mounting arrangement to rotate about an axis coincident with the patient axis 100 through an angle $\theta$. The value of the angle $\theta$ is selected according to the number of translational passes to be made past the patient. During the rotation of the source/detector, no radiation is being emitted by the source and therefore no data can be collected. During this time period in which no data is being collected, it is possible that various of the patients' organs may move. Such movement affects subsequent data collection and can result in motion artifacts in the final image. To reduce these motion artifacts, the angle $\theta$ through which the source and detector is rotated, is chosen to be an angle less than the angle $\phi$ subtended by the beam set. Once the rotational motion has been completed, the source and detector move along a second translational path 120 as indicated in FIG. 4. The source and detector arrangement is shown after rotation at a position C in FIG. 4.

Figure 5:
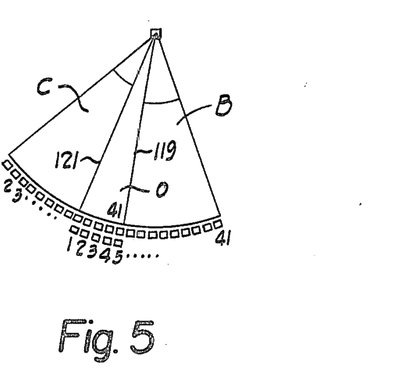
FIG. 5 shows radiation beam overlap achieved through controlled rotation of the source and detector.

FIG. 5 illustrates the beams from adjacent translations where the beams have been superimposed to illustrate an overlap portion 0. In that illustration, the overlap portion subtends five detectors. If 41 detectors comprise the array, then detectors 1-5 of the first pass will detect intensity data along path orientations identical to detectors 37-41 of the second pass. This overlapping thereby provides intensity data from identical portions of the patient cross section during different portions of the scan. Alternate translations and rotations occur until sufficient intensity data is obtained to reconstruct a computed tomography image of the cross section of interest. The redundant data readings obtained during the overlap portion are modified according to a procedure which will be described in conjunction with the reconstruction process.

To receive intensity readings from all path orientations, the source/detector pair need only be rotated through an angle of 180°. Once the pair have been rotated more than 180°, the detectors are receiving radiation which has passed through the patient field along a path traversed previously but in an opposite direction. Modification of this redundant intensity data obtained during a later portion of the scan is also performed in the reconstruction process.

From the above it is apparent that data must be modified from adjacent translations as well as widely separated translations in the scan. This is achieved by scaling appropriate intensity data readings by a weighting factor before the reconstruction process is performed. All redundant intensity readings from a given detector during a given translation are scaled by either an overlap and/or overscan weighting factor. The overlap weighting factors depends upon the overlap geometry between adjacent traverses and the overscan weighting factors depends upon detector positioning within the entire scanning rotation.

By modifying intensity data from redundant readings throughout the scan, both motion and data misalignment artifacts are reduced. The overlap weighting or scaling reduces artifacts caused by discontinuities introduced during the successive rotate portions of the scan. The overscan weighting reduces artifacts introduced from discontinuities from the beginning to the end of the scan. This scaling can be varied according to the geometrical characteristics of the scan.

Figure 6:
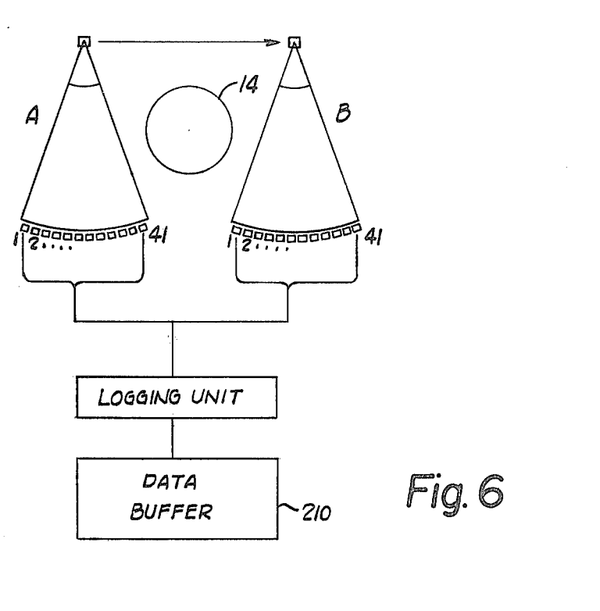
FIG. 6 illustrates the data gathering and storing technique for radiation intensity values.

FIG. 6 shows in schematic form two positions A, B of the fan shaped beam of X-radiation. Position A corresponds to a detector/source pair position at the beginning of a pass and position B represents the position at the end of a pass. The detectors are shown schematically but represent 41 detectors mounted at $\frac{1}{2}$° increments and therefore subtend an angle of $20\frac{1}{2}$° of beam spread.

Also shown in FIG. 6 is a data buffer 210 which comprises part of the signal processor shown schematically in FIG. 1. X-ray signal intensity data is sent to this buffer and stored while the detector/source pair pass the aperture 14. Data sent to the buffer is proportional to the logarithm of the X-ray intensity. The logging of the intensity is achieved in hardware separate from the buffer according to known techniques.

Once all data is stored for a given translational pass, the buffer data is sent to a disk for temporary storage. This data will be retrieved from the disk's storage when the reconstruction process is performed for each of the data gathering passes.

Figure 7:
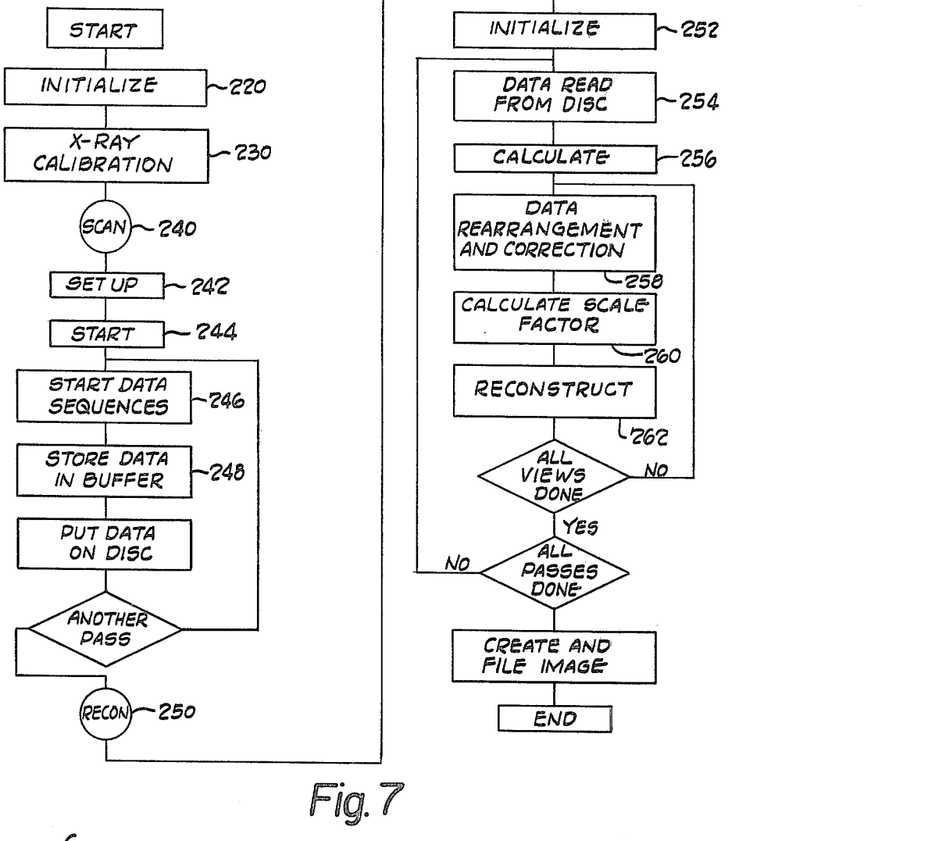
FIG. 7 is a schematic flow chart of the scanning process.

FIG. 7 depicts in schematic form a procedure for analyzing the data collected during the translate/rotate scanning process. Since certain of the steps represented are not novel and merely depict the environment in which the present invention functions, they are described in only enough detail to enable those skilled in the art to practice the invention.

A block 220 labeled Initialize, represents a number of functions performed before the scanning operation begins. During this step, the computed tomography scanning user sets up a number of parameters which are variable within the system. A second block 230 indicates that an X-ray calibration process is being performed.

While the initialize and X-calibration blocks 220, 230 represent general houskeeping and preparatory steps, the scan block 240 indicates that intensity data is actually being obtained. The scan begins when the user pushes a start button. This step is indicated by the start block 244 of the scan procedure. When the scan start button is pushed, the source and detector begin to translate relative to the field and data is collected by the detectors. This step is indicated by the block Start Data Sequences 246 of the scan process. As the source and detector translate relative to the field, data is continually being stored in the buffer unit. The details of the storage can vary without departing from the spirit of this invention and therefore this step has been shown in schematic form as Store Data In Buffer 248.

As the source and detector array move relative to the field, subsequently obtained intensity data is serially stored within the buffer unit. The scanning and storing of intensity data continues until the translation is complete. Once the translation is complete, the data is stored on disks and subsequent rotations and translations occur. The data from the next translation is stored in a similar manner upon disks. This sequence of translations and rotations continues until the scan is complete. Typically, the unit will, as a minimum scan and rotate nine times. When the scanning has been completed, all scanning intensity data is stored upon disks and is ready for reconstruction imaging.

One known technique for reconstruction imaging involves the process of convolving the initial intensity data and then back projecting that convolved data back over the field of the patient. This process produces an image of the patient density variations within the field.

The reconstruction process 250 begins with an initialization step 252. During initialization, certain tabulated data are read into the computer memory. What particular values of tabulated data are utilized depends upon the parameters that the user chose at the start of the scan. The reconstruction program for the computer is also initialized in the initialization step 252.

The actual reconstruction mechanics begin with a read step 254 which brings data from the disk into the main memory of the computer. The data is brought into the main memory one pass at a time.

A calculate step 256 determines certain physical constants for the scan such as the angle or physical position of the detector array for a particular source/detector pass or translation. The calculate step 256 is followed by a data rearrangement and correction step 258. This step corresponds to certain data bookkeeping operations performed prior to the reconstruction process.

Up to this point in the reconstruction process, the steps have been basically bookkeeping and initialization and have not involved any of the well known reconstruction algorithms. Also, up to this point, no direct calculations have been made to take into account the overlap or overscan positions of the beam.

A scale calculation step 260 is performed after these basic bookkeeping steps. It is this scale calculation step which takes into account the fact that the spread beam overlaps during certain portions of the scan. This step also includes scaling due to the overscan portion in which the scanning rotation exceeds 180°. The scale calculation is performed for each view of a particular pass.

To calculate a particular scaling value for a view, the parameters which the user put into the computer during the beginning of the scan, and the angular position of the particular view, must be known. When the input parameters and the position of the view are known, it is possible to determine whether an overscan and/or an overlap scaling factor need be computed and applied to data from that particular view.

There are many weighting schemes that can be used to handle the overlap data. One scheme is defined as follows:

Weighting factors for overlap between adjacent passes $$D_\theta = \theta_{j+1} - \theta_j$$

$$N_1' = I\left(1 - \frac{D_\theta}{\phi}\right)$$

$N_1 = 1$ for $N_1' \leq 1$ $N_1 = N_1'$ rounded off to nearest integer for $N_1' \geq 1$ $$B = D_\theta + \phi\left(\frac{N_1}{I} - 1\right)$$

$$W_i = \frac{1}{N_1}\left(\frac{\phi}{I} + \frac{BI}{2\phi} + i - 1\right) \text{ for } i = 1, 2, \ldots, N_1$$

$$W_i = \frac{1}{N_1}\left(\frac{\phi}{I} + \frac{BI}{2\phi} - i + I\right) \text{ for } i =$$

$$I - N_1 + 1, I - N_1 + 2, \ldots, I$$

where
j = pass number
$\theta_j$ = angular orientation of source/detector during jth pass
$\theta_{j+1}$ = angular orientation of source/detector during (j+1)th pass
$D_\theta$ = difference of angular orientation between the two adjacent passes
i = detector number
I = total number of detectors
$N_1$ = number of detectors in each pass whose weighting factors are affected by overlap
B = angular deviation of detector orientation in the overlap region between adjacent passes
$W_i$ = detector weighting due to overlap To illustrate the use of this weighting scheme in the preferred embodiment, let $\phi = 20.5°$ and I = 41 detectors. As an example, let $\theta_j = 20°$ and $\theta_{j+1} = 37.8°$, then $$D_\theta = 37.8° - 20° = 17.8°$$

Figure 8:
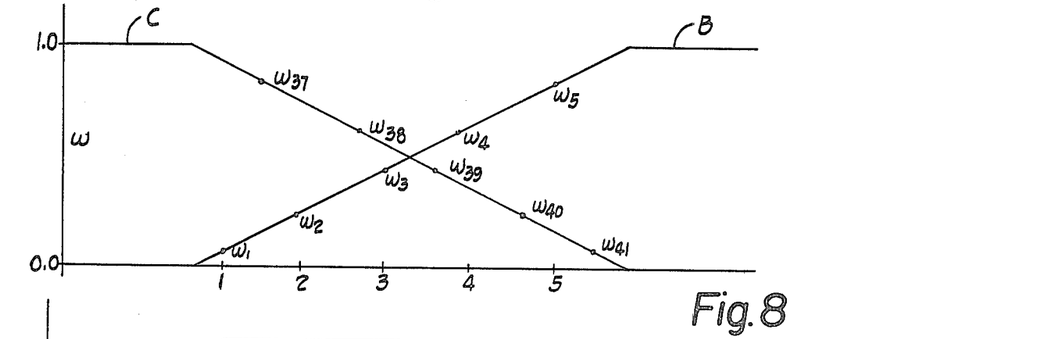
FIG. 8 illustrates a scaling procedure used in selectively weighting certain radiation intensity values.

$N_1' = 41\left(1 - \frac{17.8}{20.5}\right) = 5.4$ $N_1 = 5$ $B = 17.8 + 20.5\left(\frac{5}{41} - 1\right) = -.2°$ $W_1 = \frac{1}{5}\left[\frac{20.5}{41} - \frac{(.2)(41)}{(2)\,20.5} + 1 - 1\right] = .06$ $W_2 = 0.26$, $W_3 = 0.46$, $W_4 = 0.66$, $W_5 = 0.86$ also $W_{41} = 0.06$, $W_{40} = 0.26$, $W_{39} = 0.46$, $W_{38} = 0.66$, $W_{37} = 0.86$ FIG. 8 is a graphical illustration of the weighting factors. FIG. 8 shows the amount by which the intensity data must be reduced on those detectors for which beam overlap intensity data exists. The curve labeled B indicates the scaling or weighting factors to be applied to detector views during a given translation. The curve labled C indicates the weighting factors to be applied to detectors during the next translation.

As seen in FIG. 5, detectors 1 on the first pass and detector 37 on the second pass, receive intensity data readings from similar pass orientations. Both data readings will be utilized in the reconstruction process, but will be scaled according to the weighting factors shown in FIG. 8. Intensity data readings for view 37 on pass C will be multiplied or scaled by a weighting factor which will reduce the intensity reading to 0.86 its original value. The data reading for view 1 on the pass B will be scaled so that the intensity is reduced to a value of 0.06 its original reading. The scheme shown in FIG. 8 insures that the average value of the sum of the weighting factors is one for every ½° of overlap. It also insures the weighting or scaling factors vary from a maximum near the area of no overlap to a minimum near the edge of the fan shaped array.

Although the weighting factors shown in FIG. 8 are graphical representations, the signal processor actually performs a series of calculations to determine the exact overlap weighting factor for each view.

Figure 9:
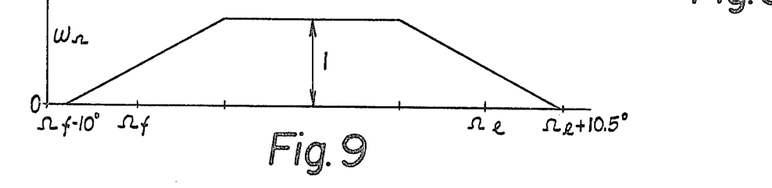
FIG. 9 shows a second scaling or weighting procedure.

If the particular detector or view being processed contains intensity readings from an orientation from which a detector earlier in the scan also obtained intensity readings, a so called overscan weighting factor is applied to that view. FIG. 9 shows a technique for applying the overscan weighting factors to a particular detector within the detector array. As was the case for the overlap weighting factor calculations, the graphical representation of FIG. 9 is illustrative of a mathematical calculation performed in the signal processor 20 to provide an overscan weighting factor. This calculation must take into account the particular geometrical design of the beam set and the scanning apparatus.

There are many different overscan weighting schemes that can be used. To illustrate one let, the position labeled $\omega_f$ in FIG. 9 indicates the orientation of the middle detector and source at the beginning of the scan. The position labeled $\omega_l$, indicates the position of the source and middle detector at the end of the scan.

Weighting Factors for Overscan $\Omega_f - \dfrac{\phi(I - 1)}{2I} = \theta_F$ = angular orientation of the first detector during the first pass $\Omega_l + \dfrac{\phi(I - 1)}{2I} = \theta_1$ = angular orientation of the last detector during the last pass $\Delta_\theta = \theta_1 - \theta_F + \dfrac{\phi}{I} - 180°$ = overscan angle $$W_{ij} = \dfrac{\theta_{ij} - \theta_F + \dfrac{\phi}{I}}{\Delta_\theta + \dfrac{\phi}{I}} \text{ for } \theta_F \leq \theta_{ij} < \theta_F + \Delta_\theta$$

where $\theta_{ij}$ = angular orientation of ith detector during jth pass
$W_{ij}$ = weighting of ith detector during jth pass $$W_{ij} = \dfrac{\theta_1 - \theta_{ij} + \dfrac{\phi}{I}}{\Delta_\theta + \dfrac{\phi}{I}} \text{ for } \theta_1 - \Delta_\theta < \theta_{ij} \leq \theta_1$$

$W_{ij} = 1$ for $\theta_F + \Delta_{74} \leq \theta_{ij} \leq \theta_1 - \Delta_{74}$ These calculations may be illustrated by a specific example. Consider a tomographic scan where $\Omega_f$ is 20° and $\Omega_l$ is 220.1°, $\phi = 20.5$, and I = 41.

$$\theta_F = 20° - \frac{(20.5)(41-1)}{(2)(41)} = 10°$$

$$\theta_1 = 220.1 + \frac{(20.5)(41-1)}{(2)(41)} = 230.1°$$

$$\Delta\theta = 230.1 - 10 + (20.5/41) - 180 = 40.6°$$

The weighting at 10° (i.e. $\theta_{ij} = 10°$) is:

$$W_{10°} = \frac{10 - 10 + \frac{20.5}{41}}{40.6 + \frac{20.5}{41}} = .012$$

$$W_{50.6°} = \frac{50.6 - 10 + \frac{20.5}{41}}{40.6 + \frac{20.5}{41}} = 1.00$$

The weighting factors for angles between 10° and 50.6° are linearly distributed between these two weighting factors:

$$W_{189.5°} = \frac{230.1 - 189.5 + \frac{20.5}{41}}{40.6 + \frac{20.5}{41}} = 1.00$$

$$W_{230.1°} = \frac{230.1 - 230.1 + \frac{20.5}{41}}{40.6 + \frac{20.5}{41}} = .012$$

The weighting factors for angle between 189.5° and 230.1° are linearly distributed between 1.00 and 0.012.

These specific illustrations define how the overscan and overlap weighting factors are determined in the signal processor 20. The angular position of the view and the input parameters are known (i.e., the geometrical specifics of the overlap and overscan are known) and thus the processor can apply an overlap and/or overscan weighting factor to that view.

The step labeled reconstruct 262 sends the weighted view data to a reconstruction processor exterior to the computer. The data is convolved and then back projected at the actual angle that the data was collected.

The weighting and reconstruction process continues until all views of a given pass have been processed. In the typical arrangement, this requires 41 views to be scaled, then convolved, and then backprojected.

Once all 41 views have been convolved and backprojected, data from another source/detector pass is read from a disk onto the computer. This data is similarly scaled, convolved, and backprojected. When this procedure has been completed for all translations or passes, the backprojected data provides a density mapping of the internal structure for a slice of the patient. This density data mapping can be projected upon a screen or a data printout to provide an examining physician information regarding the internal structure of that slice.

The scaling procedure for both the overlap and overscan portions of the scan tend to reduce motion and misalignment artifacts in this final image. These artifacts do not represent structure and, therefore, would be confusing to the physician. It should be apparent that while the scaling process has been described with regard to a particular spread shaped beam geometry, the described technique could be altered by one skilled in the art without departing from the spirit or scope of the invention as set forth in the appended claims.

What is claimed is:

1. A method for computed tomographic scanning comprising the steps of:
    (a) providing an angular spread of electromagnetic radiation that subtends an angle $\phi$;
    (b) translating said beams relative to a subject while irradiating the subject with the radiation;
    (c) measuring the intensity of the beams along various orientations after the radiation has passed through the subject and as it is translated;
    (d) rotating the source through an angle less than $\phi$, and reradiating said subject while translating the beams in their rotated orientation; the translation after rotation producing a portion of beam overlap which results in multiple intensity values for similarly oriented beam paths;
    (e) performing repeated translations and rotations until the subject has been irradiated by beams variously oriented relative to the subject, said translations and rotations defining the limits of a tomographic scan;
    (f) calculating a modified intensity for those orientations for which multiple intensity values are available; said modified intensity produced by summing of the multiple intensity values after said multiple intensity values have been scaled by a factor variable depending upon the size of beam overlap and upon the position of the orientation in the overlap; and,
    (g) constructing an image of the subject using the modified intensity.

2. A method for computed tomographic scanning comprising the steps of:
    (a) providing an angular spread of electromagnetic radiation that subtends an angle $\phi$;
    (b) translating said beams relative to a subject while irradiating the subject with the radiation;
    (c) measuring the intensity of the beams along various orientations after the radiation has passed through the subject and as it is translated;
    (d) rotating the source through an angle less than $\phi$, and reradiating said subject while translating the beams in their rotated orientation; the translation after rotation producing a portion of beam overlap which results in multiple intensity values for similarly oriented beam paths;
    (e) performing repeated translations and rotations until the subject has been irradiated by beams variously oriented relative to the subject, said translations and rotations defining the limits of a tomographic scan;
    (f) calculating a modified intensity for those orientations for which multiple intensity values are available by scaling said multiple intensities by a factor whose value depends upon the position of that orientation relative to the overlap portion, where the average of the sum of the factors is one for every one-half degree of overlap; and,
    (g) constructing an image of the subject using the modified intensity.

3. The method of claim 2 wherein the factor for an orientation varies from a maximum on the edge of the overlap portion bordering on the interior of the beam to a minimum on the edge of the overlap portion forming the outer boundary of the beam.

4. The method of claim 2 wherein the repeated rotations cause the subject to be irradiated from orientations subtending more than 180° to provide an overscan portion of beam irradiation during the scan, the orientations within the overscan portion are scaled by an overscan factor whose value depends upon the position of that orientation within the overscan portion.

5. A method of computed tomographic scanning comprising the steps of:
   (a) providing a source of electromagnetic radiation for irradiating a subject;
   (b) translating said source to irradiate the subject with radiation paths of different spatial orientations;
   (c) detecting the intensity of said variously oriented paths after said radiation has passed through the subjects;
   (d) rotating and translating the source to reradiate the subject with a plurality of reoriented radiation paths causing the subject to be scanned from orientations subtending more than 180° to provide an overscan portion of beam irradiation;
   (e) detecting the intensity of the reoriented radiation after it has passed through the subject;
   (f) repeating the rotation and translation of the source until enough intensity data is obtained for reconstructing subject density information;
   (g) scaling intensity data for those paths for which multiple intensity data is available by an overscan factor whose value depends upon the position of the multiple intensity data paths within the overscan portion to provide an adjusted intensity value; and,
   (h) computing density values within the subject from the adjusted intensity values.

6. A method of producing a representation of density variations within an interior slice of a subject by means of penetrating radiation, comprising the steps of:
   (a) producing a plurality of substantially coplanar beams of radiation, such radiation collimated into a spread of non parallel beams;
   (b) transmitting the radiation through the subject in a plane defined by the spread such that said beams traverse respective linear paths through the subject;
   (c) effecting successive translations and rotations of the spread about the subject, the rotation movement through an angle less than the angle subtended by such radiation so that as between adjacent rotational positions at least one beam of each position overlaps the spread of the previous or subsequent translation;
   (d) detecting the radiation intensity emergent from such body along each of said beam paths for each of a plurality of translational positions producing radiation intensity measurements along each path;
   (e) scaling intensity measurements for beams traversing the overlap paths according to a scheme whereby the measurements are reduced to a fraction of their unscaled values; said fraction variable depending upon the size of the successive translations and rotations and the position of said paths within said translations and rotations; and
   (f) processing the scaled intensity measurements for each of the orbital positions to produce an image reconstruction of the interior slice.

7. The method of claim 6 wherein the fraction varies from a maximum on the edge of the overlap portion bordering on the interior of the beam to a minimum on the edge of the overlap portion forming the outer boundary of the beam.

8. The method of claim 6 wherein the repeated rotations cause the subject to be irradiated from orientations subtending more than 180° to provide an overscan portion of beam irradiation during the scan, the orientations within the overscan portion are scaled by an overscan factor whose value depends upon the position of that orientation within the overscan portion.

* * * * *

UNITED STATES PATENT AND TRADEMARK OFFICE
CERTIFICATE OF CORRECTION

PATENT NO. : 4,191,892
DATED : March 4, 1980
INVENTOR(S) : Sung-Cheng Huang, Carl J. Brunnett, Rodney A. Mattson It is certified that error appears in the above-identified patent and that said Letters Patent are hereby corrected as shown below:

Column 9, line 23, before "1)" insert -- - --;

Column 10, line 39, "$w_f$" should be --$\Omega_f$--; line 41, "$w_1$" should be --$\Omega_1$--; line 65, delete "$\Delta_{74}$" and insert --$\Delta_\theta$--, both occurrences.

Signed and Sealed this

Tenth Day of June 1980

[SEAL]

Attest:

SIDNEY A. DIAMOND

Attesting Officer     Commissioner of Patents and Trademarks